(12) United States Patent
Wang et al.

(10) Patent No.: US 9,163,002 B2
(45) Date of Patent: Oct. 20, 2015

(54) METHODOLOGY FOR THE SYNTHESIS OF XANTHONES

(71) Applicants: Qian Wang, Columbia, SC (US); Jun Hu, Columbia, SC (US)

(72) Inventors: Qian Wang, Columbia, SC (US); Jun Hu, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/049,809

(22) Filed: Oct. 9, 2013

(65) Prior Publication Data

US 2014/0107354 A1    Apr. 17, 2014

Related U.S. Application Data

(60) Provisional application No. 61/795,215, filed on Oct. 12, 2012.

(51) Int. Cl.
*C07D 311/86*    (2006.01)
(52) U.S. Cl.
CPC ................. *C07D 311/86* (2013.01)
(58) Field of Classification Search
CPC ..................................................... C07D 311/86
See application file for complete search history.

(56) References Cited

FOREIGN PATENT DOCUMENTS

CN    102180858    *    9/2011

OTHER PUBLICATIONS

Chen et al., Tetrahedron 68 (2012) 8905-8907).*
Hu et al. (Chem. Comm., 2012, 48, 11256-11258).*
Hara et al. (Heterocycles (1992), 33; p. 219-228).*
Weber et al., "Phenol", Ullmann's Encyclopedia of Industrial Chemistry, Wiley-VCH, Weinheim, 2004.
Koehler et al., "Thyroid Receptor Ligands. 6. A High Affinity "Direct Antagonist" Selective for the Thyroid Hormone Receptor", J. Med. Chem. 49, 2006, 6635-6637.
Gan et al., "Structure-activity analysis of 2-modified cinnamaldehyde analogues as potential anticancer agents", Biochemical and Biophysical Research Communications 387, 2009, 741-747.
Finkelstein et al., "Tricyclic Cyanoguanidines: Synthesis, Site of Action and Insecticidal Activity of a Novel Class of Reversible Acetylcholinesterase Inhibitors", Bioorganic & Medicinal Chemistry 10, 2002, 599-613.
Rappoport, Z., "The Chemistry of Phenols", Wiley-VCH, Weinheim, 2003.
Tyman, J.H.P., "Synthetic and Natural Phenols", Elsevier, New York, 1996.
Lewis et al., "Catalytic C-C Bond Formation via Ortho-Metalated Complexes", J. Am. Chem. Soc. 108, 1986, 2728-2735.
Lyons et al., "Palladium-Catalyzed Ligand-Directed C-H Functionalization Reactions", Chem. Rev. 110, 2010, 1147-1169.
Ritleng et al., "Ru-, Rh-, and Pd-Catalyzed C-C Bond Formation Involving C-H Activation and Addition on Unsaturated Substrates: Reactions and Mechanistic Aspects", Chem. Rev. 102, 2002, 1731-1769.
Davies et al., "C-H Functionalization in organic synthesis", Chem, Soc. Rev. 40, 2011, 1855-1856.
Bedford et al., "The development of palladium catalysts for C-C and C-heteroatom bond forming reactions of aryl chloride substrates", Coordination Chemistry Reviews 248, 2004, 2283-2321.

(Continued)

*Primary Examiner* — Valerie Rodriguez-Garcia
(74) *Attorney, Agent, or Firm* — Dority & Manning, P.A.

(57) ABSTRACT

Methods are provided for forming a xanthone derivative via reacting a 2-substituted benzaldehyde with a phenol derivative to form the xanthone derivative.

13 Claims, 11 Drawing Sheets xanthone derivatives $R_1, R_2, R_3, R_4, R_6, R_7, R_8, R_9$ = aryl, alkyl, alkoxy, halide, amine, hydroxyl, nitro, cyano $R_5$ = F, Cl, Br, I, nitro, alkoxy

X = O, S, NH

(56) References Cited

OTHER PUBLICATIONS

Sengupta et al., "Recent Advances in Asymmetric Gold Catalysis", ChemCatChem 2, 2010, 609-619.
Huang et al., "Transition-metal-catalyzed C-C bond formation through the fixation of carbon dioxide", Chem. Soc. Rev. 40, 2011, 2435-2452.
Racowski et al., "C-H Bond Activation at Pailadium(IV) Centers", J. Am. Chem. Soc. 133, 2011, 18022-18025.
Zhang et al., "Combining Gold(I)/Gold(III) Catalysis and C-H Functionalization: A Formal Intramolecular [3+2] Annulation towards Tricyclic Indolines and Mechanistic Studies", Angew. Chem. Int. Ed. 50, 2011, 4450-4454.
Guo et al., "Iron-Catalyzed ortho-Selective Functionalization of Phenols: A Straightforward Strategy towards the 2'-Hydroxphenyl-1,2-dione Skeleton", Eur. J. Org. Chem. 2010, 5787-5790.
Dick et al., "A Highly Selective Catalytic Method for the Oxidative Functionalization of C-H Bonds", J. Am. Chem. Soc, 126, 2004, 2300-2301.
Desai et al., "Insights into Directing Group Ability in Palladium-Catalyzed C-H Bond Functionalization", J. Am. Chem. Soc. 130, 2008, 13285-13293.
Thu et al., "Intermolecular Amidation of Unactivated $sp^2$ and $sp^3$ C-H Bonds via Palladium-Catalyzed Cascade C-H Activation/Nitrene Insertion", J. Am. Chem. Soc. 128, 2006, 9048-9049.
Dick et al., "Carbon-Nitrogen Bond-Forming Reactions of Palladacycles with Hypervalent Iodine Reagents", Organometallics 26, 2007, 1365-1370.
Oi et al., "Rhodium-HMPT-catalyzed direct ortho arylation of phenols with aryl bromides", Tetrahedron Letters 44, 2003, 8665-8668.
Kalyani et al, "A Simple Cataiytic Method for the Regioselective Halogenation of Arenes", Organic Letters vol. 8, No. 12, 2006. 2523-2526.
Wan et al., "Highly Selective C-H Functionalization/Halogenation of Acetanilide", J. Am. Chem. Soc. 128, 2006, 7416-7417.
Chen et al., "Cu(II)-Catalyzed Functionalizations of Aryl C-H Bonds Using $O_2$ as an Oxidant" J. Am. Chem. Soc. 128, 2006, 6790-6791.
Mei et al., "$Pd^{11}$-Catalyzed Monoselective ortho Halogenation of C-H Bonds Assisted by Counter Cations: A Complementary Method to Directed ortho Lithiation", Angew. Chem. Int. Ed. 47, 2008, 5215-5219.
Inamoto et al., "Palladium-catalysed direct synthesis of benzo[b]thiophenes from thioenols", Chem. Commun. 2008, 5529-5531.
Inamoto et al., "Palladium-Catalyzed Synthesis of 2-Substituted Benzothiazoles via a C-H Functionalization/Intramolecular C-S Bond Formation Process", Organic Letters, vol. 10, No. 22, 2008, 5147-5150.
Joyce et al., "Heterocycle Formation via Palladium-Catalyzed Intramolecular Oxidative C-H Bond Functionalization: An Efficient Strategy for the Synthesis of 2-Aminobenzothiazoles", Org, Lett., vol. 11. No. 13, 2009, 2792-2795.
Zhao et al., "Palladium-Catalyzed C-H Bond Functionalization with Arylsulfonyl Chlorides", J. Am. Chem. Soc. 131, 2009, 3466-3467.
Kalyani et al., "Oxidative C-H Activation/C-C Bond Forming Reactions: Synthetic Scope and Mechanistic Insights", J. Am. Chem. Soc. 127, 2005, 7330-7331.
Deng et al., "Ruthenium-Catalyzed Oxidative Cross-Coupling of Chelating Arenes and Cycloalkanes", Angew. Chem. Ed.47, 2008, 6278-6282.
Zhao et al., "Rhodium-Catalyzed Regioselective C-H Functionalization via Decarbonylation of Acid Chlorides and C-H Bond Activation under Phosphine-Free Conditions", J. Am, Chem. Soc. 130, 2008, 8136-8137.
Tsai at al., "Asymmetric Synthesis of (-)-Incarvillateine Employing an Intramolecular Alkylation via Rh-Catalyzed Olefinic C-H Bond Activation", J. Am. Chem. Soc. 130, 2008, 6316-6317.
Giri et al., "Synthesis of 1,2- and 1,3-Dicarboxylic Acids via Pd(II)-Catalyzed Carboxylation of Aryl and Vinyl C-H Bonds", J. Am. Chem. Soc. 130, 2008, 14082-14083.
Campeau et al., "Site-Selective $sp^2$ and Benzylic $sp^3$ Palladium-Catalyzed Direct Arylation", J. Am. Chem. Soc. 130, 2008, 3266-3267.
Wu et al., "Pailadium-Catalyzed Oxidative C-H Bond Coupling of Steered Acetanilides and Aldehydes: A Facile Access to ortho-Acylacetanilides", Organic Letters vol. 13, No. 12, 2011, 3258-3261.
Satoh et al., "Palladium-catalyzed cross-carbonylation of phenolic compounds with aldehydes to give benzofuran-2(3$H$)-one derivatives", Journal of Molecular Catalysis A: Chemical 143, 1999, 203-210.
Woo at al., "Synthesis of new zanthone analogues and their biological activity test-Cytotoxicity, topoisomerase II inhibition, and DNA cross-linking study", Bioorg. Med. Chem. Lett. 17, 2007, 1163-1166.
Matsumoto et al., "Xanthones induce cell-cycle arrest and apoptosis in human colon cancer DLD-1 cells", Bioorganic & Medicinal Chemistry 13, 2005, 6064-6069.
Schwaebe et al., "Total synthesis of psorospermin", Tetrahedron Letters 46, 2005, 827-829.
Pedro et al., "Xanthones as Inhibitors of Growth of Human Cancer Cell Lines and Their Effects on the Proliferation of Human Lymphocytes In Vitro", Bioorganic & Medicinal Chemistry 10, 2002, 3725-3730.
Grover et al., "Xanthones, Part IV.* A New Synthesis of Hydroxyxanthones and Hydroxybenzophenones", J. Sci, Ind, Res., India, 13, 175, 3982-3985.
Jackson et al., "Design, Synthesis, and Pharmacological Evaluation of Potent Xanthone Dicarboxylic Acid Leukotriene $B_4$ Receptor Antagonists", J. Med. Chem. 36, 1993, 1726-1734.
Familoni et al., *Intramolecular Anionic Friedel-Crafts Equivalents. A General Regiospecific Route to Substituted and Naturally Occurring Xanthn-9-ones*. University of Waterloo P., Ontario, Sep. 1997, p. 1081-1083.
Hassall et al., "The Biosynthesis of Phenols, Part III. Oxidative Coupling leading to Geodoxin and Related Compounds", J. Chem Soc. 1961, 2312-2315.
Wang et al., "One-step preparation of xanthones via Pd-catalyzed annulation of 1,2-dibromoarenes and salicylaldehydes" Chem. Commun. 2009, 6469-6471.
Okuma et al., "Reaction of Benzyne with Salicylaldehydes: General Synthesis of Xanthenes, Xanthones, and Xanthols", Organic Letters, Vol. 11, No. 1, 2009, 169-171.
Zhao et al., "One-Pot Synthesis of Xanthones and Thioxanthones by the Tandem Coupling-Cyclization of Arynes and Salicylates", Organic Letters, vol. 7, No. 19, 4273-4275.
Zhao et al., "Synthesis of Xanthones, Thioxanthones, and Acridones by the Coupling of Arynes and Substituted Benzoates", J. Org. Chem. 72, 2007, 583-588.
Zhao et al., "An Aryl to Imidoyl Palladium Migration Process Involving Intramolecular C-H Activation", J. Am. Chem. Soc. 129, 2007, 5288-5295.
Wang et al., "Rhodium-Catalyzed Xanthone Formation from 2-Aryloxybenzaldehydes via Cross-Dehydrogenative Coupling (CDC)", Organic Letters, vol. 14, No. 3, 2012, 902-905.
Liang et al., "Characterization of Sparstolonin B, a Chinese Herb-derived Compound, as a Selective Toll-like Receptor Antagonist with Potent Anti-inflammatory Properties", The Journal of Biological Chemistry, vol. 286, No. 30, Jul. 29, 2011, p. 26470-26479.

* cited by examiner

METHODOLOGY FOR THE SYNTHESIS OF XANTHONES

PRIORITY INFORMATION

The present application claims priority to U.S. Provisional Patent Application Ser. No. 61/795,215 of Wang, et al. filed on Oct. 12, 2012, the disclosure of which is incorporated by reference herein.

BACKGROUND

Direct acylation of phenolic C—H bond usually attracts much attention since phenols are one of the most important aromatic compounds in nature and industry. Two major categories of pathways can be followed in this transformation, namely, the most well-known powerful Lewis acid-catalyzed Friedel-Crafts acylation pathway, and the transition-metal-catalyzed C—H activation pathway. However, Friedel-Crafts acylation reaction is usually difficult to control the regio- and/or mono-selectivity if no directing group is present in the benzene ring, and it often suffers from the harsh reaction condition, usage of air/water sensitive Lewis acid and incompatibility with many functional groups. Meanwhile, although transition-metal-catalyzed C—H activation can direct converting carbon-hydrogen bond into carbon-oxygen, carbon-nitrogen, carbon-halide, carbon-sulfur, or carbon-carbon bonds, till now, there is no report about C—H activation in acylation reaction of unprotected phenols. To our knowledge, only one work has been published reporting the acylation of 1-naphthol with benzaldehyde catalyzed by Pd(OAc)$_2$ in the presence of triphenylphosphine. In that paper, Miura and coworkers didn't carry out an in-depth investigation of the reaction scope, and the reaction conditions were not optimized, while they just used this reaction as a control when they synthesized benzofuran-2(3H)-ones.

Xanthones are important structural units in organic chemistry and widely presented in natural products, and their derivatives were reported to show diverse physicochemical and pharmacological properties such as antioxidants, antiinflammatory, antineoplastic, and vasodilator. Albeit many methods are available for their syntheses, most of them either require advanced starting materials, involve multistep transformations, or exotic reaction conditions, more frequently, via the Friedel-Crafts reactions. There were only a few one-step synthesis of xanthones existed in literature. For example, Larock et al. reported the one-pot synthesis of xanthones by the tandem coupling-cyclization of arynes and salicylates. The same group also reported a C—H activation approach where an arylated imidoyl palladium intermediate promoted the intramolecular arylation resulted in xanthone skeletons. Another elegant work from Li group showed that 2-aryloxy-benzaldehyde can undergo an intramolecular cross-dehydrogenative coupling reaction to form xanthones smoothly.

SUMMARY

Objects and advantages of the invention will be set forth in part in the following description, or may be obvious from the description, or may be learned through practice of the invention.

Methods are generally provided for forming a xanthone derivative via reacting a 2-substituted benzaldehyde with a phenol derivative to form the xanthone derivative. In one embodiment, the 2-substituted benzaldehyde has a structure:

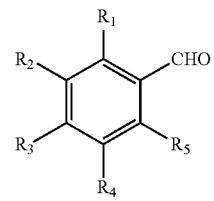

where $R_1$, $R_2$, $R_3$, and $R_4$ are, independently, H, an aryl group, an alkyl group, an alkoxy group, a halide group, an amine group, a hydroxyl group, a nitro group, or a cyano group; and where $R_5$ is F, Cl, Br, I, a nitro group, or an alkoxy group.

The phenol derivative, in one particular embodiment, has a structure:

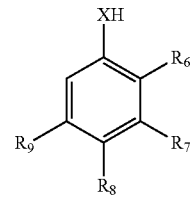

where $R_6$, $R_7$, $R_8$, and $R_9$ are, independently, H, an aryl group, an alkyl group, an alkoxy group, a halide group, an amine group, a hydroxyl group, a nitro group, or a cyano group; and X is O, S, or NH.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

Figure 1:
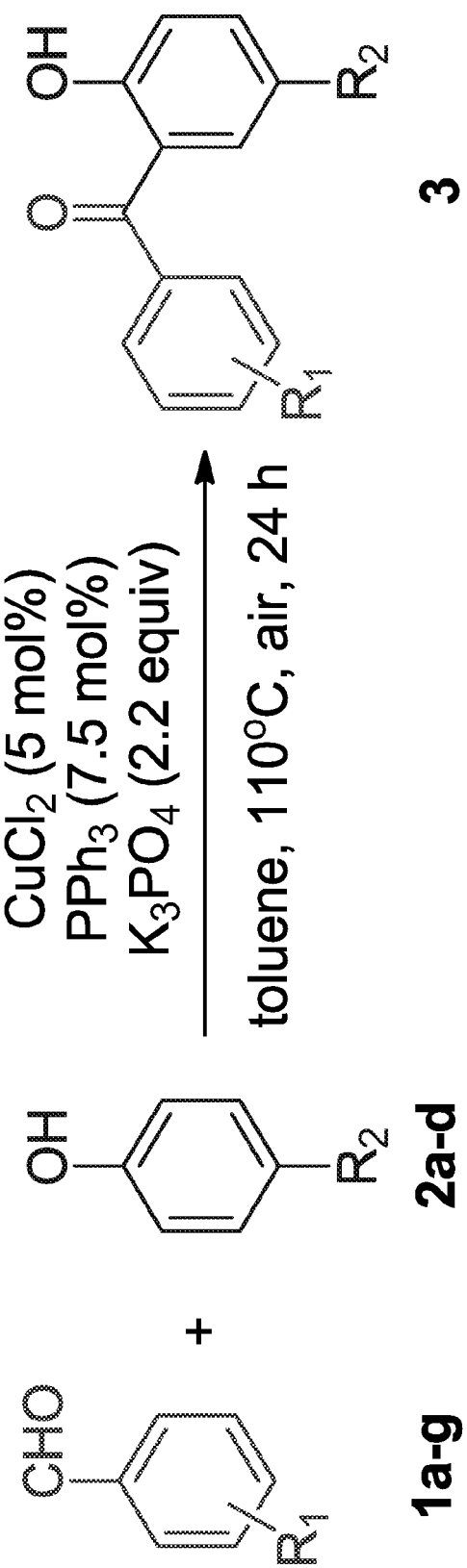
FIG. 1 shows a general schematic of a reaction for ortho-acylation of phenols with aryl aldehydes.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally speaking, the present disclosure is directed to a novel ortho-acylation reaction which can be realized with excellent yields under mild conditions. This method can be used to synthesize the xanthone derivatives. As used herein, the term "xanthone derivative" includes any molecule that has the base structure of xanthone, with or without substitutions. As such, the term "xanthone derivative" may include xanthone unless otherwise specified.

I. Acylation of Phenols with Aryl Aldehydes

In the presence of triphenylphosphine, copper (II) chloride can catalyze an intermolecular ortho-acylation reaction of phenols with aryl aldehydes. To investigate the optimized reaction protocol, a systematic screening of catalysts, ligands, and bases was carried out. Finally, we chose 1 mmol aldehyde, 1.3 mmol phenol in toluene at 110° C. in the presence of 5 mol % of $CuCl_2$, 7.5 mol % $PPh_3$ and $K_3PO_4$ (2.2 equiv.) as the standard reaction condition. However, similar reactions can also be applied.

FIG. 1 and Table 1 show, collectively, a few examples demonstrating the reaction scope of this reaction with various phenols and aryl aldehydes. The results showed that regardless of the substitution of aryl aldehydes, electron withdrawing or donating, all compounds furnished the desired ortho-acylation products in almost similar yields when reacted with the same phenol (70%-91% entries 1-7; 63%-94% entries 8-12; 42%-78% entries 13-16); even the 4-nitrobenzaldehyde produced a 70% yield (entry 12). The stronger electron-donating group phenols possessed, the more effective the acylation reactions were.

TABLE 1

Ortho-acylation of phenols with aryl aldehydes (see FIG. 1)

| entry | $R_1$ | | $R_2$ | | product | Yield (%) |
|---|---|---|---|---|---|---|
| 1 | 1a | 3-$OCH_3$ | 2a | $OCH_3$ | 3aa | 91[b] (79)[c] |
| 2 | 1b | 4-$CH_3$ | 2a | $OCH_3$ | 3ba | 70 (60) |
| 3 | 1c | H | 2a | $OCH_3$ | 3ca | 79 (64) |
| 4 | 1d | 3-Cl | 2a | $OCH_3$ | 3da | 83 (70) |
| 5 | 1e | 4-F | 2a | $OCH_3$ | 3ea | 84 (73) |
| 7 | 1f | 2,6-$OCH_3$ | 2a | $OCH_3$ | 3fa | 77 (65) |
| 8 | 1a | 3-$OCH_3$ | 2b | i-Pr | 3ab | 94 (82) |
| 9 | 1b | 4-$CH_3$ | 2b | i-Pr | 3bb | 73 (60) |
| 10 | 1c | H | 2b | i-Pr | 3cb | 63 (48) |
| 11 | 1d | 3-Cl | 2b | i-Pr | 3db | 92 (79) |
| 12 | 1g | 4-$NO_2$ | 2b | i-Pr | 3gb | 70 (58) |
| 13 | 1a | 3-$OCH_3$ | 2c | H | 3ac | 56 (47) |
| 14 | 1b | 4-$CH_3$ | 2c | H | 3bc | 64 (50) |
| 15 | 1d | 3-Cl | 2c | H | 3dc | 78 (67) |
| 16 | 1g | 4-$NO_2$ | 2c | H | 3gc | 42 (31) |
| 17[d] | 1g | 4-$NO_2$ | 2d | I | 3gd | 62 (51) |
| 18 | 1a | 3-$OCH_3$ | 2e | $NO_2$ | — | — |

[a]1 mmol aldehyde and 1.3 mmol phenol;
[b]1H NMR yield;
[c]Isolated yield;
[d]Cross-coupling reaction between iodine and hydroxyl was observed besides the ortho-acylation reaction.

II. One Step Synthesis of Xanthone Derivatives

Figure 2:
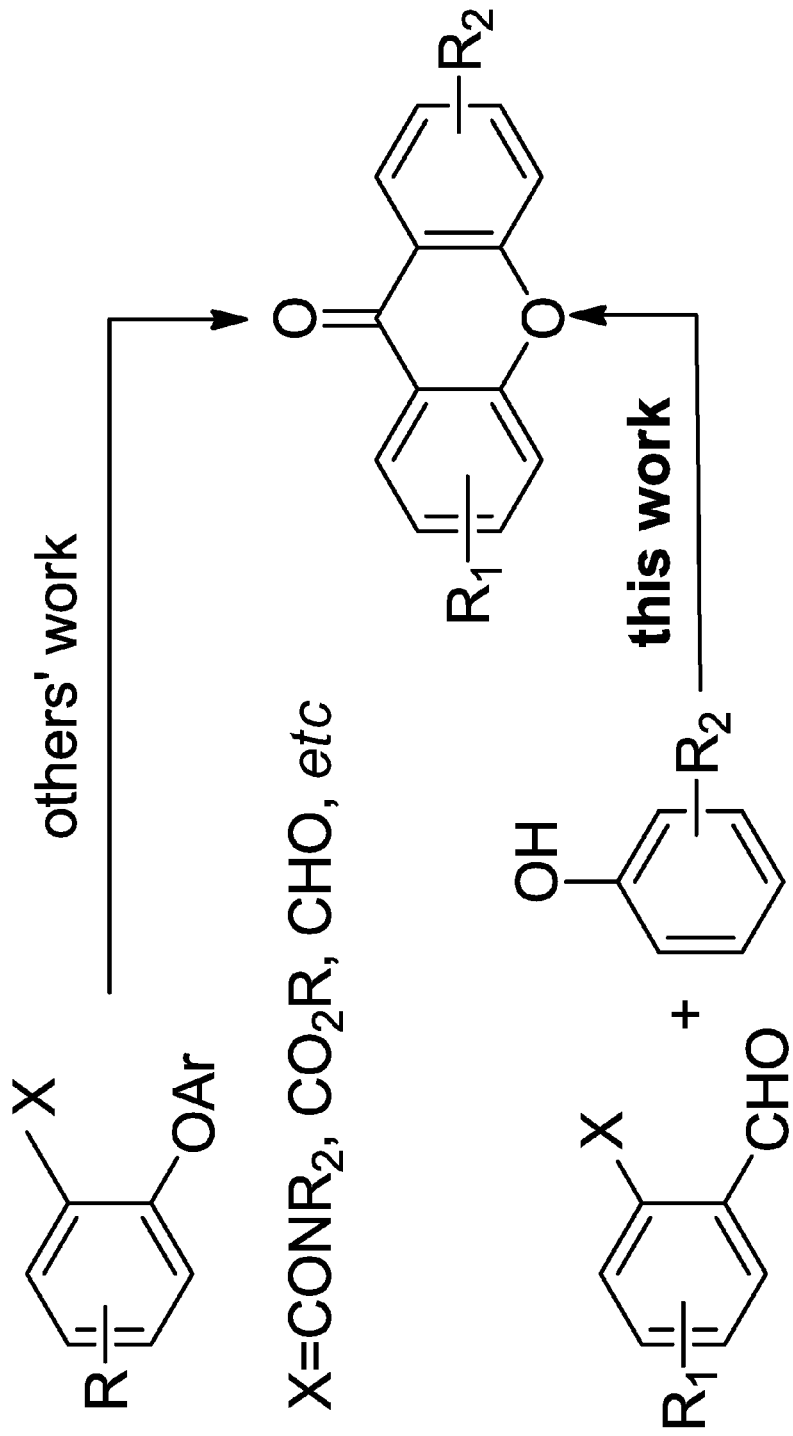
FIG. 2 shows a general schematic of different reaction methods for one step synthesis of xanthone derivatives.
Figure 3:
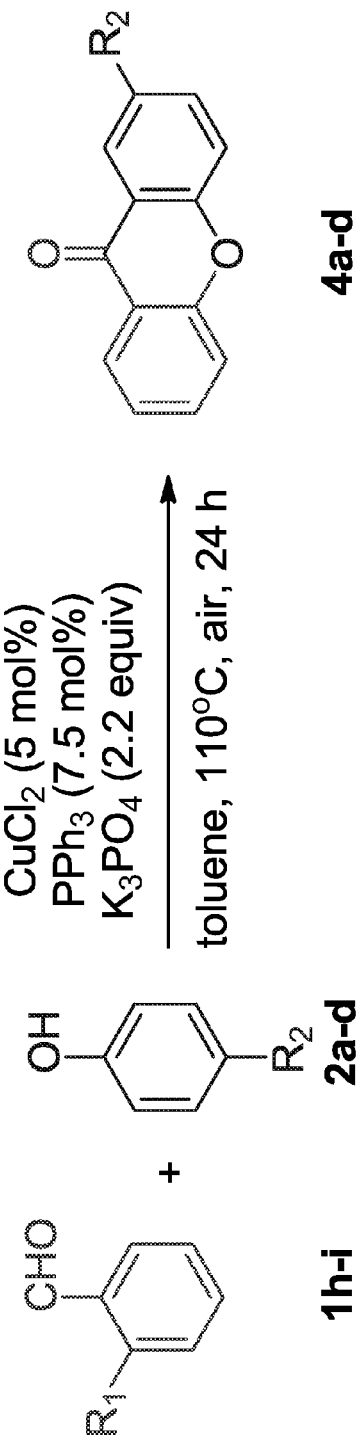
FIG. 3 shows a general schematic of an exemplary reaction method for one step synthesis of a xanthone derivative.

It was found that when 2-substituted aryl aldehyde (1h-j) reacted with phenols, xanthones were obtained with high-yield in one step (see, FIG. 3 and Table 2, collectively). Albeit many methods are available for the synthesis of xanthones, most of them either require advanced starting materials, exotic reaction conditions, or involve multistep transformations. There are only a few one-step synthesis of xanthones existing in literature. Hence, the presently disclosed method offers a concise and straightforward strategy to construct xanthones directly without the preactivation of aldehydes (see FIG. 2).

A. Exemplary Reactions

As shown in FIG. 3 and Table 2, 2-methoxybenzaldehyde (1h) and 2-nitrobenzaldehyde (1i) produced the corresponding xanthones in excellent yields (entries 1, 2, 4, 6 and 8), while with 2-bromobenzaldehyde (1j) as the starting material, lower yields were observed, likely due to the cross-coupling reaction between bromo and hydroxyl groups (entries 3, 5 and 7, yields are listed in the footnote). It is believed that the ring-closed xanthone products are achieved via the ortho-acylation of phenols with 2-substituted aryl aldehydes first, and then under a basic condition, the ortho-substituents of aldehydes serving as leaving groups lead to the final ring-closed xanthones.

TABLE 2

One-step ortho-acylation of phenols with 2-substituted benzaldehydes to afford xanthones[a] (see FIG. 3)

| entry | $R_1$ | | $R_2$ | | product | Yield % |
|---|---|---|---|---|---|---|
| 1 | 1h | $OCH_3$ | 2a | $OCH_3$ | 4a | 85[b] (71)[c] |
| 2 | 1i | $NO_2$ | 2a | $OCH_3$ | 4a | 87 (74) |
| 3[d] | 1j | Br | 2a | $OCH_3$ | 4a | 68 (52) |
| 4 | 1i | $NO_2$ | 2b | i-Pr | 4b | 92 (81) |
| 5[d] | 1j | Br | 2b | i-Pr | 4b | 64 (56) |
| 6 | 1i | $NO_2$ | 2c | H | 4c | 81 (70) |
| 7[d] | 1j | Br | 2c | H | 4c | 55 (43) |
| 8 | 1i | $NO_2$ | 2d | I | 4d | 73 (62) |

[a]1 mmol 2-substitued aldehydes and 1.3 mmol phenol;
[b]1H NMR yield;
[c]Isolated yield;
[d]Cross-coupling reaction between bromo and hydroxyl was observed in entries 3 (17%), 5 (14%) and 7 (13%) besides the ortho-acylation reaction.

Figure 4:
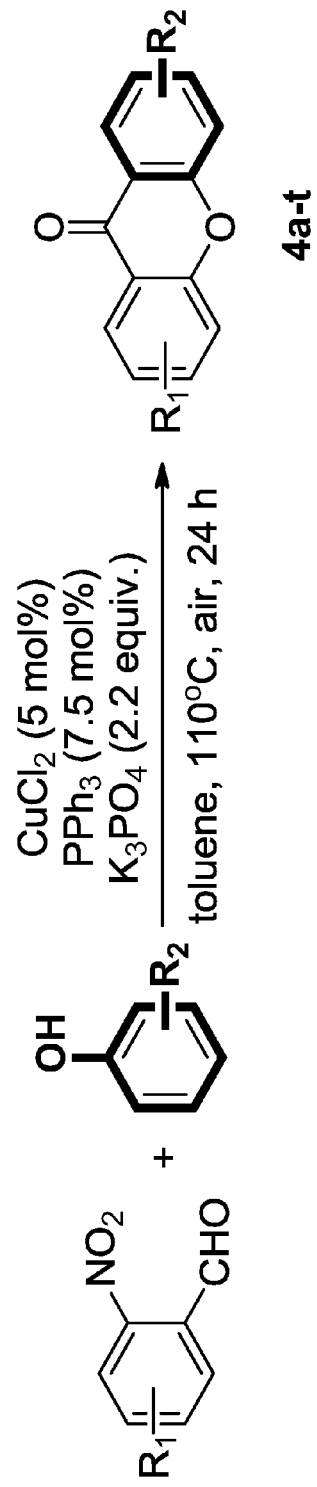
FIG. 4 shows a general schematic of an exemplary reaction method for one step synthesis of a xanthone derivative.

Since nitro group gave better results than other leaving groups, the reaction substrates of 2-nitrobenzaldehydes and phenols were investigated (FIG. 4 and Table 3, collectively). It showed that alkoxy, alkyl, aryl and halide substituents were tolerated on the phenols to furnish the desired xanthones affording moderate to excellent yields. While electron-donating groups on phenols can promote the reaction, electron-withdrawing groups ($NO_2$ or CN) will block the reaction completely (data not shown). If the substituted group was at the para position of the phenol, the yield was higher than it was at ortho position, possibly due to the steric effect (4d vs 4e, 4g vs 4h). The steric effect can also explain the excellent regioselectivity of this reaction (e.g. 4i was the sole product) as was as the sluggish reactivity of ortho-t-butylphenol (no product was observed). Disubstituted and trisubstituted xanthones could also be prepared via this copper-catalyzed ortho-acylation reaction affording moderate yields (4m-p and 4t).

TABLE 3

Scope of reaction of 2-nitrobenzaldehydes with phenols to prepare xanthones[a]

| Product | | Yield (%) |
|---|---|---|
| 4a | (xanthone-OMe) | 87[b](74)[c] |
| 4b | (xanthone-iPr) | 92(81) |
| 4c | (xanthone) | 81(70) |
| 4d | (xanthone-I) | 77(62) |
| 4e | (xanthone-I) | 73(62) |
| 4f | (xanthone-Br) | 72(59) |
| 4g | (xanthone-Cl) | 82(73) |

TABLE 3-continued

Scope of reaction of 2-nitrobenzaldehydes with phenols to prepare xanthones[a]

| Product | | Yield (%) |
|---|---|---|
| 4h | (xanthone-Cl) | 76(60) |
| 4i | (xanthone-F) | 70(58) |
| 4j | (xanthone-F) | 71(55) |

| Product | | Yield[b] (%) |
|---|---|---|
| 4k | (xanthone-Ph) | 69(55) |
| 4l | (naphtho-xanthone) | 43(30) |
| 4m | (xanthone-Cl,Cl) | 75(64) |
| 4n | (xanthone-Me,Me) | 84(72) |

TABLE 3-continued

Scope of reaction of 2-nitrobenzaldehydes with phenols to prepare xanthones[a]

| | | |
|---|---|---|
| 4o | | 90(80) |
| 4p | | 73(61) |
| 4q | | 83(70) |
| 4r | | 82(70) |
| 4s | | 80(69) |
| 4t | | 68(57) |

[a] 1 mmol 2-nitrobenzaldehydes, 1.3 mmol phenols;
[b] 1H NMR yield;
[c] Isolated yield.

B. Extension of Reaction Methods to Other Synthesis

Figure 5:
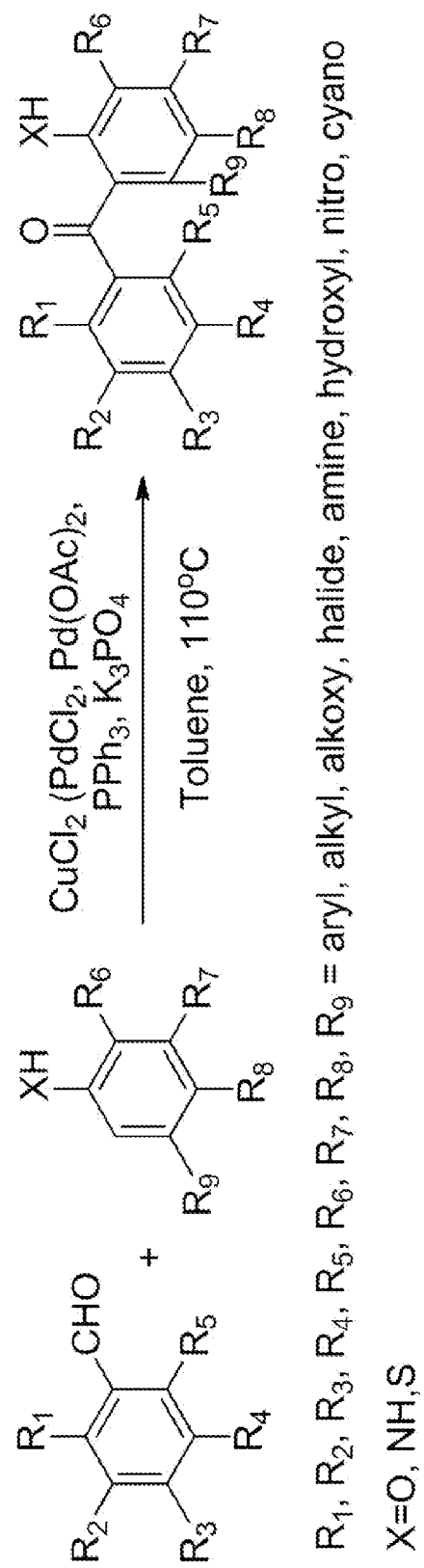
FIG. 5 shows a general schematic of an exemplary intermolecular ortho-acylation reaction of phenols with aryl aldehydes.
Figure 6:
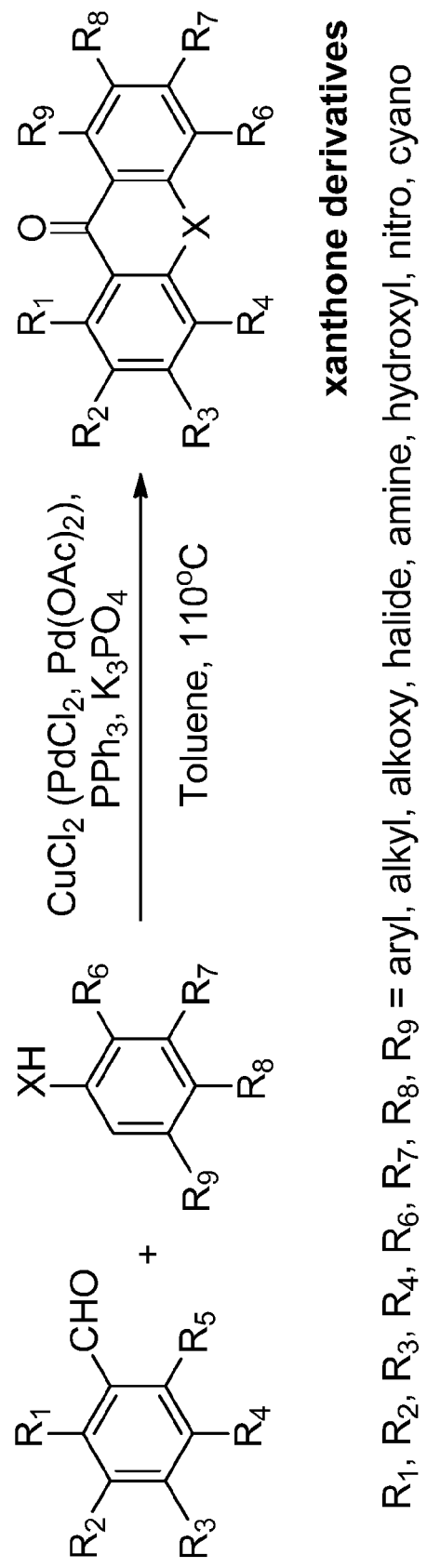
FIG. 6 shows a general schematic of an exemplary reaction method for one step synthesis of a xanthone derivative.

As show in FIG. 5, through the optimization of the reaction condition, we chose the system of 5 mol % of $CuCl_2$, $PdCl_2$, or $Pd(OAc)_2$, 7.5 mol % $PPh_3$, $K_3PO_4$ (2.2 equiv.) and the substrates in toluene at 110° C. as our standard reaction condition. However, this condition can be adjusted based on the structural diversity of different substrates. Using this system, a series of ortho-acylation derivatives of phenols and xanthone derivatives have been synthesized with high yields (FIGS. 5 and 6).

In conclusion, we have demonstrated the catalytic intermolecular ortho-acylation of phenols with various aryl aldehydes using copper/palladium as the catalyst in presence of the triphenyl-phosphine ligand, and it can be used to synthesize xanthone derivatives in one step with high yields.

Our reaction condition is considerably mild, and it offers an alternative to the widely used Lewis acid-catalyzed Friedel-Crafts acylation reaction that often suffers from the harsh reaction condition, usage of air/water sensitive Lewis acid and incompatibility with many functional groups.

C. 2-Substituted Benzaldehydes

In view of the above discussion, particularly suitable 2-substituted benzaldehydes have a structure of Formula I below:

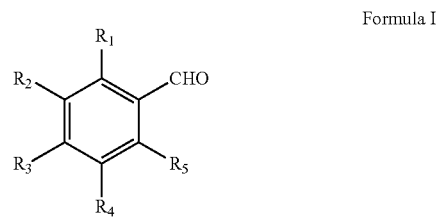

Formula I where $R_1$, $R_2$, $R_3$, and $R_4$ are, independently, H, an aryl group, an alkyl group, an alkoxy group, a halide group, an amine group, a hydroxyl group, a nitro group, or a cyano group; and where $R_5$ is F, Cl, Br, I, a nitro group, or an alkoxy group.

In particular embodiments, $R_5$ is a nitro group, and/or at least three of $R_1$, $R_2$, $R_3$, and $R_4$ are H (i.e., leaving only a single organic group extending from the ring). Such a benzaldehyde compound is shown in Formula II:

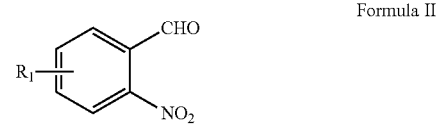

Formula II where $R_1$ is H, an aryl group, an alkyl group, an alkoxy group, a halide group, an amine group, a hydroxyl group, a nitro group, or a cyano group.

D. Phenol Derivatives

Particularly suitable phenol derivatives have a structure of Formula III below:

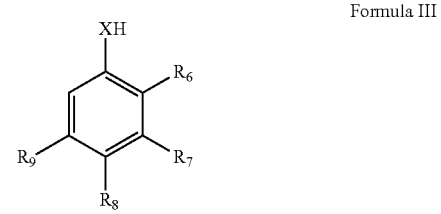

Formula III where $R_6$, $R_7$, $R_8$, and $R_9$ are, independently, H, an aryl group, an alkyl group, an alkoxy group, a halide group, an amine group, a hydroxyl group, a nitro group, or a cyano group; and X is O, S, or NH.

In particular embodiments, X is O, and/or at least three of $R_6$, $R_7$, $R_8$, and $R_9$ are H (i.e., leaving only a single organic group extending from the ring). Such a compound is shown in Formula IV:

Formula IV

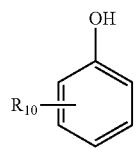

where $R_{10}$ is H, an aryl group, an alkyl group, an alkoxy group, a halide group, an amine group, a hydroxyl group, a nitro group, or a cyano group.

E. Reaction Conditions

The molar ratio of aldehydes to phenols can be about 1:1 to about 1:5, such as about 1.25 to about 1.35 (e.g., about 1:1.3). Generally, the triphenylphosphine is used as a ligand to the catalyst. In certain embodiments, the 2-substituted benzaldehyde is reacted with the phenol derivative in the presence of a catalyst system including a palladium catalyst (e.g., $PdCl_2$, $Pd(OAc)_2$, etc.) and a copper catalyst (e.g., $CuCl_2$). The ratio of these catalysts to the phenol can be about 2 mol % to about 10 mol % (e.g., about 5 mol %) Generally, the $K_3PO_4$ is used as the base for deportonation. All these experiments were carried out in an inert atmosphere (e.g., under the protection of nitrogen).

F. Xanthone Derivatives

Generally, the reaction of the 2-substituted benzaldehyde of Formula I with the phenol derivative of Formula III results in the formation of a xanthone derivative having the structure of Formula V:

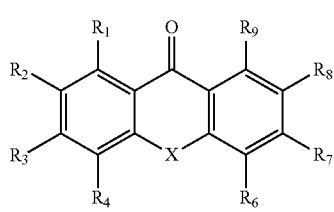

Formula V where $R_1$, $R_2$, $R_3$, $R_4$, $R_6$, $R_7$, $R_8$, and $R_9$ remain unchanged from their parent compounds described above (i.e., the 2-substituted benzaldehyde of Formula I and the phenol derivative of Formula III).

Figure 7A:
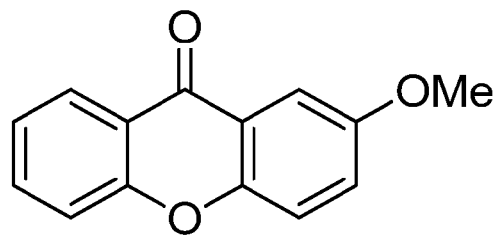
FIGS. 7A-7T show exemplary xanthone derivatives formed according to the Examples.
Figure 7B:
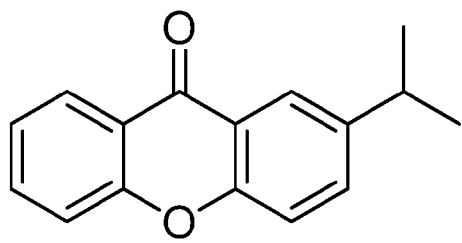
Figure 7C:
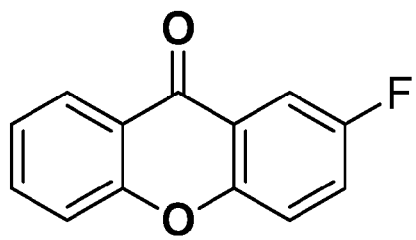
Figure 7D:
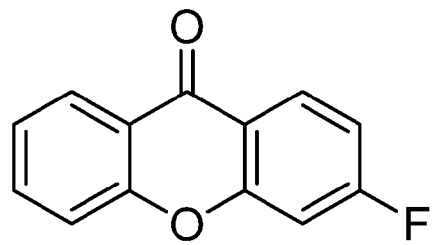
Figure 7E:
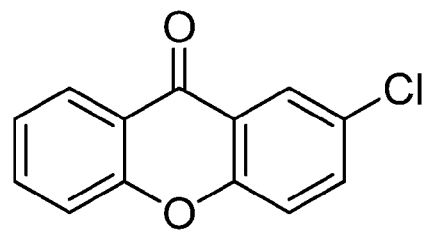
Figure 7F:
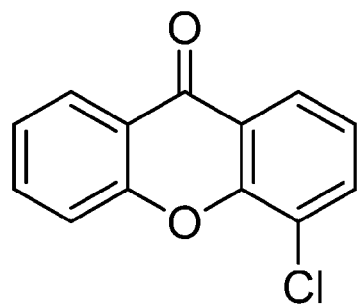
Figure 7G:
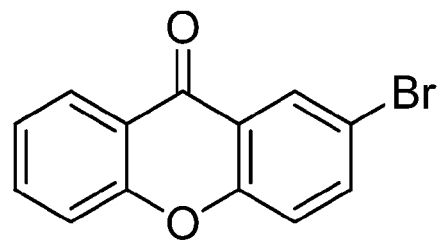
Figure 7H:
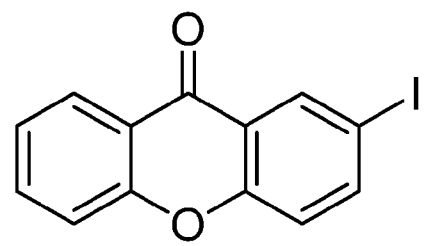
Figure 7I:
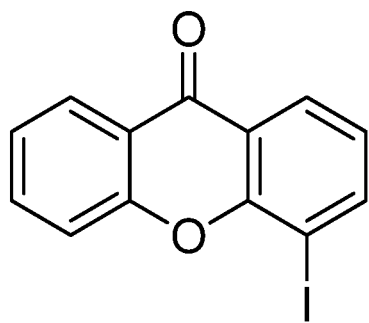
Figure 7J:
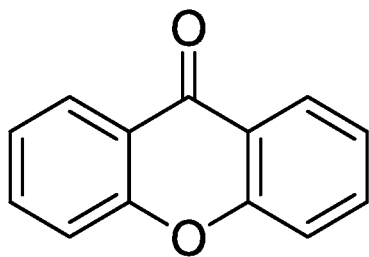
Figure 7K:
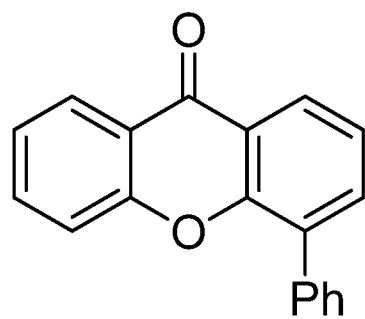
Figure 7L:
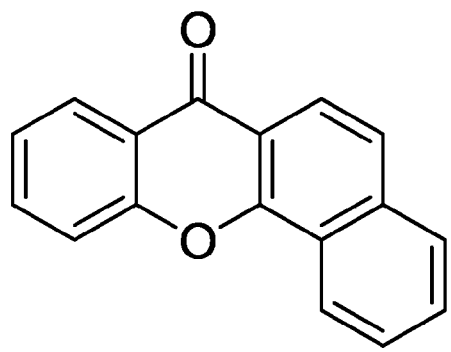
Figure 7M:
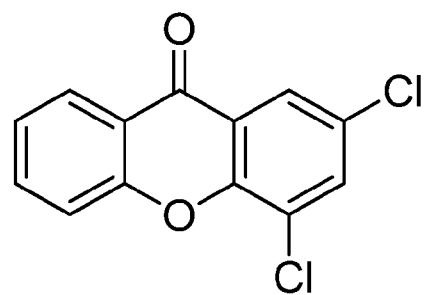
Figure 7N:
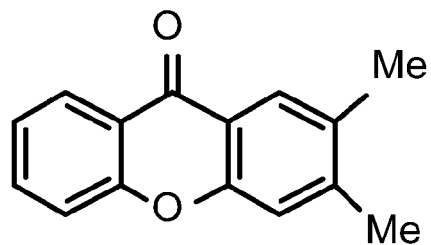
Figure 7O:
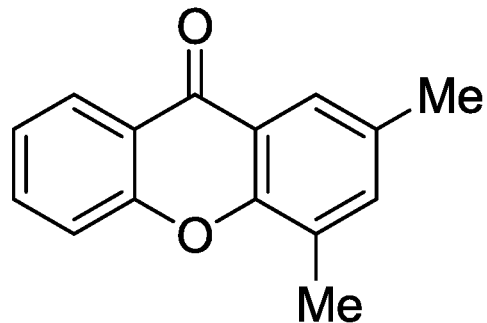
Figure 7P:
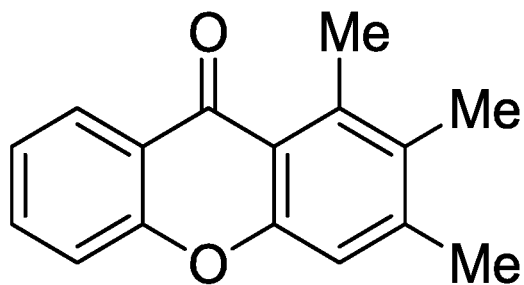
Figure 7Q:
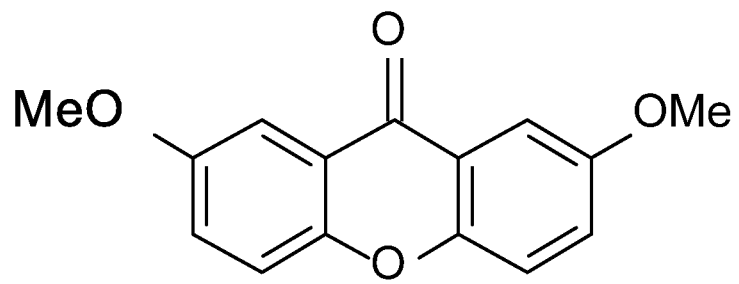
Figure 7R:
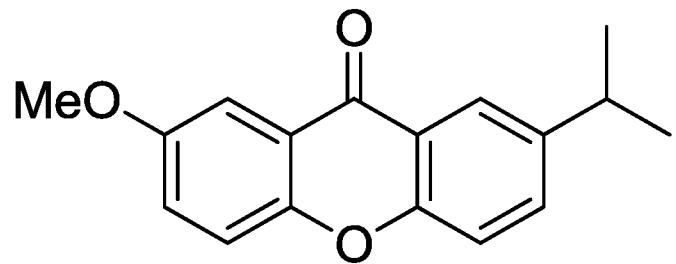
Figure 7S:
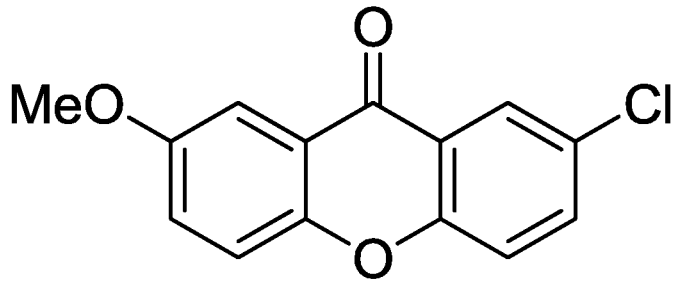
Figure 7T:
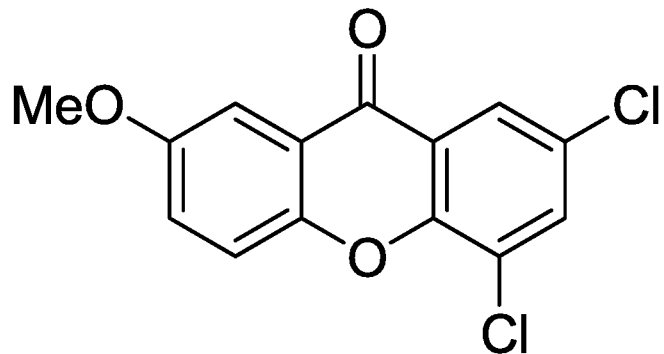

FIGS. 7A-7T show particularly suitable xanthone derivatives that can be formed (with "Me" representing a methyl group, as is commonly used in the art).

EXAMPLES

General One-Pot Experimental Procedure for Synthesis of Ortho-Acylation Products Phenols/Thiophenol (1.3 equiv), aldehydes (1 equiv.), $K_3PO_4$ (2.2 equiv.), $CuCl_2$, $PdCl_2$ or $Pd(OAc)_2$ (5 mol %) and $PPh_3$ (7.5 mol %) were added in 3 mL toluene, and then the reaction stirred at 110° C. for 24 h. The mixture was extracted with DCM, washed by water, brine, and then the combined organic layer was dried by anhydrous $Na_2SO_4$. After evaporation of solvents, the crude product was purified by flash chromatography to afford ortho-acylation derivatives.

General One-Pot Experimental Procedure for Synthesis of Xanthone Derivatives 2-nitro/halides/alkoxy substituted-Phenols/Thiophenol (1.3 equiv), aldehydes (1 equiv.), $K_3PO_4$ (2.2 equiv.), $CuCl_2$, $PdCl_2$ or $Pd(OAc)_2$ (5 mol %) and $PPh_3$ (7.5 mol %) were added in 3 mL toluene, and then the reaction stirred at 110° C. for 24 h. The mixture was extracted with DCM, washed by water, brine, and then the combined organic layer was dried by anhydrous $Na_2SO_4$. After evaporation of solvents, the crude product was purified by flash chromatography to afford xanthone derivatives.

Xanthone derivatives having the general structures shown in FIGS. 7A-7T were made according to the above described method. Each structure was confirmed by $^1$HNMR, $^{13}$C NMR, and MS data.

These and other modifications and variations to the present invention may be practiced by those of ordinary skill in the art, without departing from the spirit and scope of the present invention, which is more particularly set forth in the appended claims. In addition, it should be understood that the aspects of the various embodiments may be interchanged both in whole or in part. Furthermore, those of ordinary skill in the art will appreciate that the foregoing description is by way of example only, and is not intended to limit the invention so further described in the appended claims.

The invention claimed is:

1. A method of forming a xanthone derivative, the method comprising: reacting a 2-substituted benzaldehyde with a phenol derivative in the presence of a catalyst system including a palladium catalyst and a copper catalyst to form the xanthone derivative;

wherein the 2-substituted benzaldehyde has a structure;

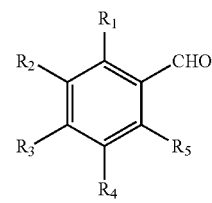

where $R_1$, $R_2$, $R_3$, and $R_4$ are, independently, H, an aryl group, an alkyl group, an alkoxy group, a halide group, an amine group, a hydroxyl group, a nitro group, or a cyano group; and where $R_5$ is F, Cl, Br, I, a nitro group, or an alkoxy group; and wherein the phenol derivative has a structure:

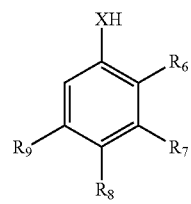

where $R_5$, $R_7$, $R_3$, and $R_9$ are, independently, H, an aryl group, an alkyl group, an alkoxy group, a halide group, an amine group; a hydroxyl group, a nitro group, or a cyano group; and X is O, S, or NH, and wherein the xanthone derivative formed has a structure:

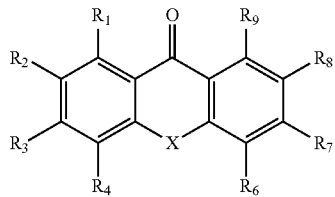

where $R_1$, $R_2$, $R_3$, $R_4$, $R_6$, $R_7$, $R_8$, $R_9$ are as defined above.

2. The method of claim 1, wherein $R_5$ is a nitro group.

3. The method of claim 1, wherein at least three of $R_1$, $R_2$, $R_3$, and $R_4$ are H.

4. The method of claim 3, wherein only three of $R_1$, $R_2$, $R_3$ and $R_4$ are H and the only one that is not H is selected from an aryl group, an alkyl group, an alkoxy group, a halide group, an amine group, a hydroxyl group, a nitro group, or a cyano group.

5. The method of claim 1, wherein the 2-substituted benzaldehyde has a structure:

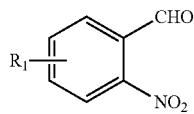

where $R_1$ is H, an aryl group, an alkyl group, an alkoxy group, a halide group, an amine group, a hydroxyl group, a nitro group, or a cyano group.

6. The method of claim 5, wherein $R_1$ is an aryl group, an alkyl group, an alkoxy group, a halide group, an amine group, a hydroxyl group, a nitro group, or a cyano group.

7. The method of claim 1, wherein at least three of $R_6$, $R_7$, $R_8$, and $R_9$ are H.

8. The method of claim 7, wherein only three of $R_6$, $R_7$, $R_8$ and $R_9$ are H and the only one that is not H is selected from an aryl group, an alkyl group, an alkoxy group, a halide group, an amine group, a hydroxyl group, a nitro group, or a cyano group.

9. The method of claim 1, wherein X is O.

10. The method of claim 1, wherein the phenol derivative has a structure:

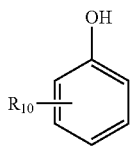

where $R_{10}$ is H, an aryl group, an alkyl group, an alkoxy group, a halide group, an amine group, a hydroxyl group, a nitro group, or a cyano group.

11. The method of claim 10, wherein $R_{10}$ is an aryl group, an alkyl group, an alkoxy group, a halide group, an amine group, a hydroxyl group, a nitro group, or a cyano group.

12. The method of claim 1, wherein the 2-substituted benzaldehyde is reacted with the phenol derivative in the presence of triphenylphosphine.

13. The method of claim 1, wherein the xanthene derivative is selected from the group consisting of:

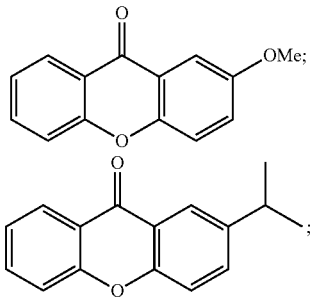

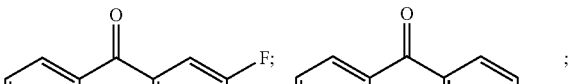

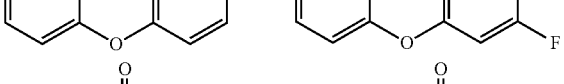

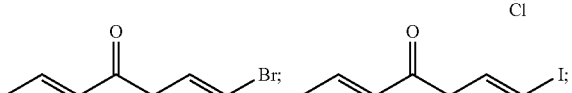

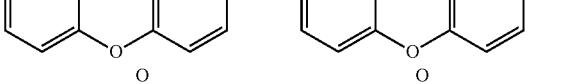

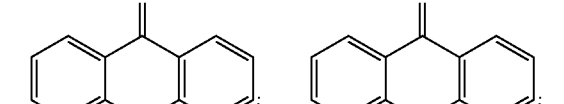

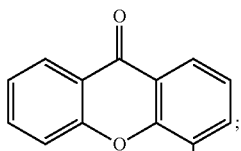

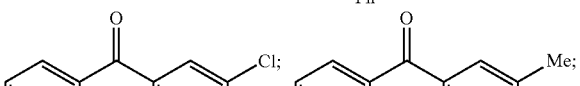

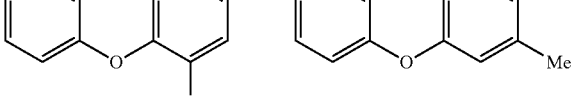

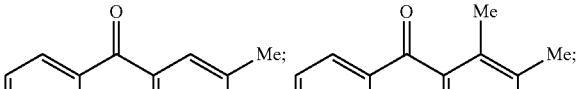

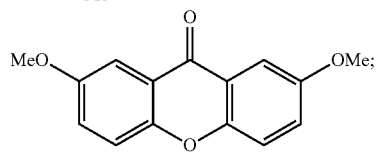

-continued
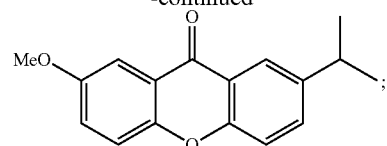
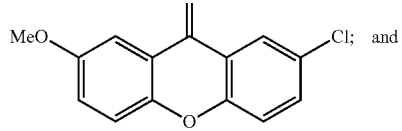
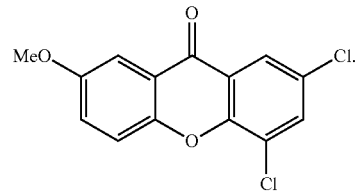
* * * * *